（12） United States Patent
Smith

(10) Patent No.: US 10,702,491 B2
(45) Date of Patent: *Jul. 7, 2020

(54) SOAP COMPOSITIONS AND METHODS

(71) Applicant: Vanguard Soap LLC, Memphis, TN (US)

(72) Inventor: Scott A. Smith, Memphis, TN (US)

(73) Assignee: Vanguard Soap LLC, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/847,034

(22) Filed: Dec. 19, 2017

(65) Prior Publication Data

US 2018/0104206 A1  Apr. 19, 2018

Related U.S. Application Data

(63) Continuation of application No. 15/197,553, filed on Jun. 29, 2016, now Pat. No. 9,844,524.

(60) Provisional application No. 62/186,089, filed on Jun. 29, 2015.

(51) Int. Cl.

| | | |
|---|---|---|
| *A61K 31/20* | (2006.01) | |
| *C11D 9/38* | (2006.01) | |
| *C10M 105/24* | (2006.01) | |
| *C11D 17/04* | (2006.01) | |
| *C10M 117/02* | (2006.01) | |
| *C10M 129/32* | (2006.01) | |
| *C10M 129/40* | (2006.01) | |
| *C11D 9/00* | (2006.01) | |
| *C11D 9/48* | (2006.01) | |

(52) U.S. Cl.
CPC ............ *A61K 31/20* (2013.01); *C10M 105/24* (2013.01); *C10M 117/02* (2013.01); *C10M 129/32* (2013.01); *C10M 129/40* (2013.01); *C11D 9/007* (2013.01); *C11D 9/38* (2013.01); *C11D 9/48* (2013.01); *C11D 17/049* (2013.01); *C10M 2207/122* (2013.01); *C10M 2207/1203* (2013.01); *C10M 2207/125* (2013.01); *C10M 2207/126* (2013.01); *C10M 2207/128* (2013.01); *C10M 2207/1225* (2013.01); *C10M 2207/1256* (2013.01); *C10M 2207/1265* (2013.01); *C10M 2207/1285* (2013.01); *C10M 2207/401* (2013.01); *C10N 2210/01* (2013.01); *C10N 2220/025* (2013.01); *C10N 2220/026* (2013.01); *C10N 2230/16* (2013.01); *C10N 2270/00* (2013.01)

(58) Field of Classification Search
CPC ........ A61K 31/20; C11D 9/38; C11D 17/044; C11D 9/007; C11D 9/48; C10M 117/02; C10M 129/32; C10M 129/14; C10M 2207/1203; C10M 2207/122; C10M 2207/1225; C10M 2207/125; C10M 2207/1256; C10M 2207/126; C10M 2207/1265; C10M 2207/128; C10M 2207/1285; C10M 2207/401; C10N 2210/01; C10N 2220/025; C10N 2220/026; C10N 2230/16; C10N 2270/00
See application file for complete search history.

(56) References Cited

U.S. PATENT DOCUMENTS 4,118,407 A * 10/1978 Red .................... C11B 13/02
554/178

FOREIGN PATENT DOCUMENTS

| WO | WO 2006128555 | * | 7/2006 |
|---|---|---|---|
| WO | WO 2013076047 | * | 5/2013 |

* cited by examiner

*Primary Examiner* — Shirley V Gembeh
(74) *Attorney, Agent, or Firm* — Buler Snow LLP

(57) ABSTRACT

Natural soap compositions and methods of manufacturing the same having anti-microbial properties for treating and preventing diaper rash and other microbial infections. The soap compositions may contain one or more fatty acids with carbon length ranging from four (C4) to twenty-two (C22) and/or natural fatty acid mixtures of coconut oil, olive oil, and/or tall oil fatty acids which are saponified with lye. The saponification lye may be sodium or potassium hydroxide. In preferred embodiments, the soap compositions contain at least one of sodium or potassium caprate, sodium or potassium caprylate, or mixtures thereof, especially 55:45% caprylate to caprate. The soap compositions are effective at treating or preventing diaper rashes and other microbial infections associated with *Candida albicans* (Ca—yeast), *Pseudomonas aeruginosa* (Psa—a Gram negative bacteria), *Staphylococcus aureus* (Sa—a Gram positive bacteria), and *Aspergillus niger* (An—a mold).

19 Claims, No Drawings

SOAP COMPOSITIONS AND METHODS

CROSS-REFERENCE TO RELATED APPLICATIONS

This application is a continuation of U.S. Pat. No. 9,844,524 granted on Dec. 19, 2017 which claims the benefit of U.S. Provisional Application No. 62/186,089 to Scott A. Smith filed on Jun. 29, 2015, the contents of which are incorporated herein by reference in its entirety.

FIELD OF THE INVENTION

The present invention is generally directed towards soap compositions and methods for manufacturing soap compositions from various carbon chain length fatty acids, and more specifically to C8 and C10 fatty acid-containing soaps and methods of manufacturing the same.

BACKGROUND OF THE INVENTION

Soap can be defined as a salt of one or more of the higher fatty acids with an alkali or metal. Most soaps are made by the action of potassium or sodium hydroxide on animal fats and vegetable oils (or fatty acids). The preparation of soap directly from the raw fatty acids by the use of a lye (either potassium or sodium hydroxide) is referred to as saponification, which is well known in the art of soap manufacture.

Because soaps are generally compatible with antimicrobial agents, they are often used in antimicrobial washes. Such soap-based antimicrobial washes are found in numerous products used to treat diaper rash including wipes, creams, lotions, and liquid and solid soaps and cleansers. Diaper rash is a condition which is, in its most simple stages, a contact dermatitis. The most commonly accepted list of factors linked to diaper rash includes ammonia, microbial agents (certain bacteria, molds, and the yeast *Candida albicans*m), the products of bacterial action, urine pH, and moisture. Generally, the current products available to treat diaper rash or daily maintenance of diaper rash sensitive areas are expensive and contain synthetic chemical fragrances and artificial colorants.

There is a need for a cost effective soap made with all natural products that will effectively treat and prevent diaper rash or other skin infections caused by microbial agents.

SUMMARY OF THE INVENTION

Accordingly, it is an object of the present invention to provide novel soap compositions and methods that overcome these and other problems of the prior art by providing soap compositions used to treat and prevent diaper rash, other skin disorders, and for use in industrial applications. In one aspect, the present invention provides a method of manufacturing a soap composition comprising the step of saponifying one or more fatty acids ranging in carbon length from four (C4) to twenty-two (C22). In some embodiments, the fatty acids comprise a mixture of fatty acids ranging in carbon length from four (C4) to twenty-two (C22). In some embodiments, natural fatty acid mixtures of coconut oil, olive oil, tallow, tall oil fatty acids, sunflower oil, and/or safflower oil are used. In some preferred embodiments, the fatty acids comprise at least caprylate (C8). In other preferred embodiments, the fatty acids comprise at least caprate (C10). In still other preferred embodiments, the fatty acids comprise at least caprylate (C8), caprate (C10), or mixtures thereof. The step of saponification may be performed by adding lye in some embodiments. In preferred embodiments, the lye is either sodium or potassium hydroxide.

In another aspect, the present invention provides a soap composition comprising one or more saponified fatty acids ranging in carbon length from four (C4) to twenty-two (C22). In some embodiments, the fatty acids comprise a mixture of fatty acids ranging in carbon length from four (C4) to twenty-two (C22). In some embodiments, natural fatty acid mixtures of coconut oil, olive oil, tallow, tall oil fatty acids, sunflower oil, and/or safflower oil are used. In some preferred embodiments, the fatty acids comprise at least caprylate (C8). In other preferred embodiments, the fatty acids comprise at least caprate (C10). In still other preferred embodiments, the fatty acids comprise at least caprylate (C8), caprate (C10), or mixtures thereof. In some preferred embodiments, the saponified fatty acids are prepared with sodium or potassium hydroxide. In preferred embodiments the soap composition comprises at least potassium caprylate (C8). In other preferred embodiments, the soap composition comprises at least potassium caprate (C10). In still other preferred embodiments, the soap composition comprises at least potassium caprylate (C8), potassium caprate (C10), or mixtures thereof.

In another aspect, the present invention provides a soap composition in various administration forms, such as soaps (liquid, solid, or foaming cleansers), wipes, and lotions comprising an effective amount of potassium caprylate (C8) or potassium caprate (C10) for treating or preventing microbial agents that cause diaper rash or other skin infections. In some embodiments, the soap composition comprises an effective amount of potassium caprylate (C8), potassium caprate (C10), or mixtures thereof for treating or preventing a diaper rash or other skin infections associated with one or more of the group of microbial agents consisting of *Candida albicans* (Ca—yeast), *Pseudomonas aeruginosa* (Psa—a Gram negative bacteria), *Staphylococcus aureus* (Sa—a Gram positive bacteria), and *Aspergillus niger* (An—a mold). In preferred embodiments, the soap composition comprises an effective amount of potassium caprylate (C8), potassium caprate (C10), or mixtures thereof for treating or preventing a diaper rash or other skin infections associated with *Candida albicans* (Ca—yeast). In still other embodiments, the soap composition comprises an effective amount of potassium caprylate (C8), potassium caprate (C10), or mixtures thereof for cleaning, deodorizing, and/or disinfecting countertops, commercial/industrial work surfaces, and/or metal surfaces.

In still another aspect, the present invention provides a method of treating or preventing a diaper rash or other skin infections by administering an effective amount of a soap composition comprising potassium caprylate (C8), potassium caprate (C10), or mixtures thereof. In some embodiments, the diaper rash is associated with one or more of the group of microbial agents consisting of *Candida albicans* (Ca—yeast), *Pseudomonas aeruginosa* (Psa—a Gram negative bacteria), *Staphylococcus aureus* (Sa—a Gram positive bacteria), and *Aspergillus niger* (An—a mold). In preferred embodiments, the diaper rash or other skin infection is associated with *Candida albicans* (Ca—yeast).

DETAILED DESCRIPTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

The present invention provides novel soap compositions and methods that overcome the problems of the prior art discussed above, as well as others. While the embodiments are discussed herein as being directed toward soap compositions and methods used to treat and prevent diaper rash or other skin infections, a person of skill in the art would appreciate that the present invention's soap compositions and methods can be used to treat and prevent a variety of microbial infections by cleansing or treating (applying) the skin and/or hair of a subject in need thereof. For example, a subject in need thereof can be an animal with exposure to or susceptibility to a microbial infection or transfer on or from its skin and/or hair (fur). In preferred embodiments, a subject in need thereof is a person with an exposure to or susceptibility to a microbial infection on the skin, such as a diaper rash.

Thus, in one aspect, the present invention provides a method of manufacturing a soap composition comprising the step of saponifying one or more fatty acids ranging in carbon length from four (C4) to twenty-two (C22). In some embodiments, the fatty acids comprise a mixture of fatty acids ranging in carbon length from four (C4) to twenty-two (C22). In some embodiments, natural fatty acid mixtures of coconut oil, olive oil, tallow, tall oil fatty acids, sunflower oil, and/or safflower oil are used. In some preferred embodiments, the fatty acids comprise at least caprylate (C8). In other preferred embodiments, the fatty acids comprise at least caprate (C10). In still other preferred embodiments, the fatty acids comprise at least caprylate (C8), caprate (C10), or mixtures thereof. The step of saponification may be performed by adding lye. Any saponifying counter ion can be used in some embodiments. In preferred embodiments, the lye is either sodium or potassium hydroxide. The saponified fatty acids (soap) are foaming water soluble natural soaps that are mild to the skin and have excellent color, clarity, and odor. They may then be processed with other soaps, detergents, natural fragrances, and/or pigments/adjuvants that are well known in the field or other processing for preparing commercial soaps, shampoos, wipes, lotions, or creams for use by a subject in need thereof to create a further soap composition of the invention. The soaps exemplified herein are particularly suited for personal care application like hand washes, body washes, shampoos, and bubble baths and can be in the form of a hand soap, a liquid hand soap, a foaming liquid hand soap, a bath gel, an exfoliate cleanser, a cleaning wipe, a shampoo, a lotion, or a cream. They are also excellent additives for deodorizing and disinfecting cleaners, pet care products, hard surface cleaners (such as for countertops, commercial surfaces, industrial surfaces, and/or metal surfaces), and industrial lubrication applications.

In another aspect, the present invention provides a soap composition comprising one or more saponified fatty acids ranging in carbon length from four (C4) to twenty-two (C22). In some embodiments, the fatty acids comprise a mixture of fatty acids ranging in carbon length from four (C4) to twenty-two (C22). In some embodiments, natural fatty acid mixtures of coconut oil, olive oil, tallow, tall oil fatty acids, sunflower oil, and/or safflower oil are used. In some preferred embodiments, the fatty acids comprise at least caprylate (C8). In other preferred embodiments, the fatty acids comprise at least caprate (C10). In still other preferred embodiments, the fatty acids comprise at least caprylate (C8), caprate (C10), or mixtures thereof. The fatty acids ranging in carbon length from four (C4) to twenty-two (C22) or natural oils of coconut oil, olive oil, tallow, tall oil fatty acids, sunflower oil, and/or safflower oil are saponified by addition of a lye or other appropriate counter ion to create the saponified fatty acids. In some preferred embodiments, the saponified fatty acids are prepared with sodium or potassium hydroxide as the lye. In preferred embodiments the soap composition comprises at least potassium caprylate (C8). In other preferred embodiments, the soap composition comprises at least potassium caprate (C10). In still other preferred embodiments, the soap composition comprises at least potassium caprylate (C8), potassium caprate (C10), or mixtures thereof. The saponified fatty acids (soap) compositions may be foaming water soluble natural soaps that are mild to the skin and have excellent color, clarity, and odor. They may then be processed with other soaps, detergents, natural fragrances, natural pigments, and/or adjuvants that are well known in the field or other processing for preparing commercial soaps, shampoos, wipes, lotions, or creams for use by a subject in need thereof to create a further soap composition of the invention. The soaps exemplified herein are particularly suited for personal care application like hand washes, body washes, shampoos, and bubble baths and can be in the form of a hand soap, a liquid hand soap, a foaming liquid hand soap, a bath gel, an exfoliate cleanser, a cleaning wipe, a shampoo, a lotion, or a cream. They are also excellent additives for deodorizing and disinfecting cleaners, pet care products, hard surface cleaners (such as for countertops, commercial surfaces, industrial surfaces, and/or metal surfaces), and industrial lubrication applications.

The present invention provides soap compositions in various administration forms, such as soaps (liquid, solid, or foaming cleansers), wipes, and lotions comprising an effective amount of potassium caprylate (C8), sodium caprylate (C8), potassium caprate (C10), sodium caprate (C10), or mixtures thereof for treating or preventing microbial agents that cause skin infections in a subject in need thereof. A person of skill in the art would appreciate that an effective amount of potassium caprylate (C8), sodium caprylate (C8), potassium caprate (C10), sodium caprate (C10), or mixtures thereof will depend on the formulation, the amount of saponified fatty acid in the formulation available to the treated area on the subject in need thereof, the area and size of the area to be treated, the surface to be treated, and/or other factors. Using well known scientific methods, a person of skill in the art will readily appreciate how to determine an effective amount of the soap compositions without undue experimentation. Other active or non-active ingredients can be included in the soap compositions.

In some embodiments, the soap compositions comprise an effective amount of potassium caprylate (C8), sodium caprylate (C8), potassium caprate (C10), sodium caprate (C10), or mixtures thereof for treating or preventing an infection on a skin surface of a subject in need thereof. In some embodiments, the soap compositions comprise an effective amount of potassium caprylate (C8), sodium caprylate (C8), potassium caprate (C10), sodium caprate (C10), or mixtures thereof for treating or preventing (on a person in need thereof) a diaper rash or other skin infection associated with one or more of the group of microbial agents consisting of *Candida albicans* (Ca—yeast), *Pseudomonas aeruginosa*

(Psa—a Gram negative bacteria), *Staphylococcus aureus* (Sa—a Gram positive bacteria), and *Aspergillus niger* (An—a mold). In preferred embodiments, the soap composition comprises an effective amount of potassium caprylate (C8), sodium caprylate (C8), potassium caprate (C10), sodium caprate (C10), or mixtures thereof for treating or preventing a diaper rash or other skin infection (on a person in need thereof) associated with *Candida albicans* (Ca—yeast).

In still another aspect, the present invention provides methods of or treating or preventing an infection on a skin surface of a subject in need thereof by administering an effective amount of a soap composition comprising potassium caprylate (C8), sodium caprylate (C8), potassium caprate (C10), sodium caprate (C10), or mixtures thereof. The soap composition can be produced in various administration forms, such as soaps (liquid, solid, or foaming cleansers), wipes, creams, and lotions. The administration form can be selected based on the administration needs of the subject. Soaps, shampoos, and body washes can be used to cleanse the treatment area, for example, while bathing. Wipes, creams, and lotions can be applied to cleanse (e.g., wipes) or as an application intended for longer durations (e.g., wipes, creams, and lotions). A person of skill in the art can use any of known methods to formulate the soap compositions of the present invention into any of the various administration forms.

The soap composition is administered by applying an effective amount of the soap composition onto the skin or hair (fur) of a subject in need thereof, or on the surface of an object in need thereof. The step of administration can be repeated (administration regimen) as often as required by the particular conditions of the subject (or surface) in need thereof. For example, an administration regimen may be once a day to six or more times per day or once per a specified event (e.g., changing of a diaper) to once per hour. Administration regimens can be determined based on the need of the subject, such as the severity of the skin infection/rash, such as severe versus moderate diaper rash, or the susceptibility of the subject to skin infection/rash, such as wearing a diaper. In some embodiments, the present invention provides a method of treating or preventing a diaper rash or other skin infection on a person in need thereof by administering an effective amount of a soap composition comprising potassium caprylate (C8), sodium caprylate (C8), potassium caprate (C10), sodium caprate (C10), or mixtures thereof. In some embodiments, the diaper rash or other skin infection is associated with one or more of the group of microbial agents consisting of *Candida albicans* (Ca—yeast), *Pseudomonas aeruginosa* (Psa—a Gram negative bacteria), *Staphylococcus aureus* (Sa—a Gram positive bacteria), and *Aspergillus niger* (An—a mold). In preferred embodiments, the diaper rash or other skin infection is associated with *Candida albicans* (Ca—yeast).

Example 1—Method of Manufacture

Manufacturing soaps comprising C8 and C10 soaps has proven difficult to achieve in a consistent clear particulate free form. The following example provides the general procedure used to achieve consistent clear particulate free form for C8 and C10 soaps. The process also results in clear particulate free form of other soaps made from various fatty acids and natural oils. To a reaction flask equipped with agitation, heat, thermometer, and nitrogen sparge is added the specified amount of fatty acid and or natural oil(s). Next the specified mass (e.g., number of grams) of potassium hydroxide reactant is added under good agitation with and without a nitrogen sparge. Next is added enough water to make the final product have a solids content of 30-60% by weight. This can be determined by monitoring the reaction as water is added. Nitrogen sparge, when utilized, is simply nitrogen gas bubbled through the liquid contents of the flask at a rate low enough not to produce too much foam and a rate high enough to keep the color light by minimizing oxidation. While nitrogen sparge is not required in the method, it is advantageous to use in reactions containing base oils or fatty acids of carbon chain length having a susceptibility to oxidation in order to prevent color bodies from building. The reaction mass is heated to 90-105° C. and is held for 2-5 hours.

Testing for the %-free alkali follows the reaction progress. Once the theoretical value is reached, the reaction is terminated. When the reaction is terminated, the free alkalinity is then neutralized to an acceptable pH and/or alkalinity range with an acceptable neutralizing agent. A person of ordinary skill in the art will understand that an acceptable pH and/or alkalinity range may depend on the intended use of the final product (e.g., hand soap, antiseptic cleaning soap, shampoo, bath gel, etc.) with most having an alkaline pH. All simple and blended sample compositions were tested over a range of pH from 8.8 to 13.5, with the optimum range being from 9.5 to 10.2 for liquid soap applications. Upon neutralization to an acceptable pH and/or alkalinity, the product is preferably used without additional purification or processing. For the purpose of these examples hydrochloric acid and citric acid were utilized for neutralization; however, those skilled in the art may use other neutralizing agents without departing from the spirit and scope of the invention. With each Sample (see TABLE 1), multiple simple and blended compositions of the fatty acids/oils below were assembled to achieve optimization for different applications. The percent solids of these blends were tested at a range of 18.0% (weight) to 75% (weight), with the optimum being in the range of 38.5% (weight) to 41.5% (weight) for liquid soap applications. Lower percent solids may be possible with the addition of chloride (added as either solid or in liquid solution) to thicken the soap compositions (see U.S. patent application Ser. No. 15/197,456 entitled Potassium Soaps That Can Be Thickened with Chloride Salts filed Jun. 29, 2016 by S. Smith; which is hereby incorporated by reference in its entirety for all that it teaches).

TABLE 1

| Sample | Fatty Acid and or Oil Name | Carbon Chain |
|---|---|---|
| 1 | Butyric/Caproic | C4/C6 |
| 2 | Caprylic | C8 |
| 3 | Capric | C10 |
| 4 | Caprylic/Capric | C8/C10 |
| 5 | Lauric | C12 |
| 6 | Myristic | C14 |
| 7 | Lauric/Myristic | C12/C14 |
| 8 | Palmitic | C16 |
| 9 | Stearic | C18 |
| 10 | Oleic | C18:1 |
| 11 | Ricinoleic | C18:1(OH) |
| 12 | Behenic/Eurucic | C22/C22:1 |
| 13 | Coconut Oil | Whole Oil Distribution |
| 14 | Olive Oil | Whole Oil Distribution |
| 15 | Tall Oil Fatty Acid | Whole Oil Distribution |

Example 2—C8 and C10 Fatty Acid Soap Efficacy Against *C. albicans*

First Experiment:

Absorbent materials soaked in a 55:45 mix of C8:C10 soap (Chemical SAS-10-145) were tested with *C. albicans* (often called a zone inhibition technique test). *Candida albicans* ATCC 12031 was used in this test and grown on plates of Mueller Hinton Agar. Mueller Hinton plates were inoculated with *C. albicans* to produce a lawn of growth. A portion of each of the absorbent materials (labeled as A, B, C, D, A1, B1, C1, D1, where X1 samples were negative controls) was aseptically cut into circular pieces as close to 6 mm in diameter as possible and placed on the inoculated plates. The plates were incubated for 24-48 hours at 35° C.

Zones of inhibitions were measured in mm on the plates after the incubation time period. The results are as follows: A: 25 mm; A1: 0 mm; B: 25 mm; B1: 0 mm; C: 15 mm; C1: 0 mm; D: 20 mm; and D1: 0 mm.

Second Experiment:

*Candida albicans* ATCC 12031 was used in this test and grown in Brain Heart Infusion Broth (BHI), 10 ml. Plating was done on Sabouraud Dextrose (Sab) agar plates and Tryptic Soy agar plates. Butterfield Buffer 9 ml tubes were also used. New sub-culture of *C. albicans* was prepared from lyophilized discs placed in Brain Heart Infusion Broth and incubated at 35° C. for 24 hours. *C. albicans* cultures were then transferred to Tryptic Soy agar plates and incubated for 24 hr at 35° C. Isolated colonies of were picked (with a sterile applicator stick) from these plates and resuspended in sterile De-ionized water to equal a McFarland Standard 0.5 (approximately $1.5 \times 10^8$ cfu/ml). Chemical SAS-10-145 (35% solution: 350 mg/ml) was diluted in BHI to yield a solution containing 33.98 mg/ml. This solution was further diluted in BHI to yield concentrations (mg/ml) of 16.9, 11.32, 9.71, 5.66, and 3.09. *C. albicans* cultures were then streaked to Mueller Hinton agar plates to yield a complete lawn of growth on the agar surface. The tubes of varying concentrations of SAS-10-145 were inoculated with 0.2 ml of inoculum described above. 0.1 ml of the inoculum was transferred to a Sab plate and spread over the agar surface with a sterile inoculating loop and incubated at 35° C. for 24 hours. The tubes of SAS-10-145 plus *C. albicans* were incubated at 35° C. Samples of these tubes were inoculated to Sab plates at different times to determine the killing rate of the chemical. 0.1 ml was inoculated to the plates. The results are shown in TABLE 2. The procedure was repeated for certain samples and time incubations with the results shown in TABLE 3.

TABLE 2

| Time | 33.98 mg/ml | 16.9 mg/ml | 11.32 mg/ml | 9.71 mg/ml | 5.66 mg/ml | 3.09 mg/ml |
|---|---|---|---|---|---|---|
| 0 | NG 72 hrs | NG 72 hrs | NG 72 hrs | NG 72 hrs | NG 72 hrs | NG 72 hrs |
| 1 hr | NG 72 hrs | NG 72 hrs | NG 72 hrs | NG 72 hrs | NG 72 hrs | NG 72 hrs |
| 2 hr | NG 72 hrs | NG 72 hrs | NG 72 hrs | NG 72 hrs | NG 72 hrs | NG 72 hrs |
| 5 hr | NG 72 hrs | NG 72 hrs | NG 72 hrs | NG 72 hrs | NG 72 hrs | NG 72 hrs |
| 7 hr | NG 72 hrs | NG 72 hrs | NG 72 hrs | NG 72 hrs | NG 72 hrs | NG 72 hrs |
| 16 hr | NG 72 hrs | NG 72 hrs | NG 72 hrs | NG 72 hrs | NG 72 hrs | NG 72 hrs |
| 21 hr | NG 72 hrs | NG 72 hrs | NG 72 hrs | NG 72 hrs | NG 72 hrs | NG 72 hrs |
| 26 hr | NG 72 hrs | NG 72 hrs | NG 72 hrs | NG 72 hrs | NG 72 hrs | NG 72 hrs |
| Control | >1000 cfu | >1000 cfu | >1000 cfu | >1000 cfu | >1000 cfu | >1000 cfu |

NG = no growth

TABLE 3

| Time | 11.32 mg/ml | 9.71 mg/ml | 5.66 mg/ml | 3.09 mg/ml |
|---|---|---|---|---|
| 0 | NG 72 hrs | NG 72 hrs | 7 cfu | 3 cfu |
| 2 hr | NG 72 hrs | NG 72 hrs | NG 72 hrs | NG 72 hrs |
| 4 hr | NG 72 hrs | NG 72 hrs | NG 72 hrs | NG 72 hrs |
| 8 hr | NG 72 hrs | NG 72 hrs | NG 72 hrs | NG 72 hrs |
| 10 hr | NG 72 hrs | NG 72 hrs | NG 72 hrs | NG 72 hrs |
| 23 hr | NG 72 hrs | NG 72 hrs | NG 72 hrs | NG 72 hrs |
| Control | >1000 cfu | >1000 cfu | >1000 cfu | >1000 cfu |

NG = no growth

Third Experiment:

To confirm the Experiment 2 results, three Sab plates were inoculated (as in the procedure above). The procedure set up as 1 drop and 2 drops of SAS-10-145 added to two of the inoculated plates, individually. The third Sab plate served as a control with no SAS-10-145 drops. The results are as follows: no SAS-10-145 plate had complete lawn of growth; 1 drop SAS-10-145 plate: 47 mm zone of inhibition; 2 drops SAS-10-145 plate: 48 mm zone of inhibition.

Fourth Experiment:

A suspension of *C. albicans* was prepared in Butterfield Buffer, and the suspension culture was inoculated on a Sab plate using a sterile cotton tipped applicator as a control. Then, 0.5 ml of SAS-10-145 (19.4 mg/ml) was added to the tube with *C. albicans*. A Sab plate after 1, 5, 15, and 60 minutes exposure to the SAS-10-145 was inoculated. The results are as follows: 0 time: >1000 cfu; 1 minute: 13 cfu; 5 minutes: No growth; 15 minutes: No growth; 60 minutes: No growth.

Example 3—Butyric and Caproic Acid Sample Formulation

A sample composition including both butyric fatty acid (C4) and caproic fatty acid (C6) according to the teachings above was prepared. The composition comprised about 12.6% (weight) butyric fatty acid and about 17.9% (weight) caproic fatty acid. Potassium hydroxide was included at about 10.4% (weight). The remaining material in the batch was mostly water. Sufficient citric acid (citrate) was added to neutralize the pH to an acceptable level as discussed above. Compositions following this general formulation (with and without modifications) can be used in applications of deodorizing and disinfecting hard surfaces, skin, and hair (fur). Also, heavy duty cleaning applications for metal surfaces and other industrial surfaces. The viscosity of the composition can be modified by various additives, including chlorides during the manufacturing process, to provide desirable look and feel for customer expectations. Preferably, the batch is not processed further before packaging for consumption.

Example 4—Caprylic and/or Capric Acid Sample Formulation 1

A sample composition including either or both caprylic fatty acid (C8) and capric fatty acid (C10) according to the teachings above was prepared. The composition comprised about 30.5% (weight) total of caprylic fatty acid and/or capric fatty acid. Potassium hydroxide was included at about 10.4% (weight). The remaining material in the batch was mostly water. Sufficient citric acid (citrate) was added to neutralize the pH to an acceptable level as discussed above. Compositions following this general formulation (with and without modifications) can be used in applications of deodorizing and disinfecting hard surfaces, skin, and hair (fur). Also, heavy duty cleaning applications for metal surfaces and other industrial surfaces. The viscosity of the composition can be modified by various additives, including chlorides during the manufacturing process, to provide desirable look and feel for customer expectations. Preferably, the batch is not processed further before packaging for consumption.

Example 5—Caprylic and Capric Acid Sample Formulation 2

A sample composition including both caprylic fatty acid (C8) and capric fatty acid (C10) according to the teachings above was prepared. The composition comprised about 12% to about 15% (weight) of caprylic fatty acid and about 12% to about 15% (weight) of capric fatty acid. Potassium hydroxide was included at about 10.4% (weight). The remaining material in the batch was mostly water. Sufficient citric acid (citrate) was added to neutralize the pH to an acceptable level as discussed above. Compositions following this general formulation (with and without modifications) can be used in applications of deodorizing and disinfecting hard surfaces, skin, and hair (fur). Also, heavy duty cleaning applications for metal surfaces and other industrial surfaces. The viscosity of the composition can be modified by various additives, including chlorides during the manufacturing process, to provide desirable look and feel for customer expectations. Preferably, the batch is not processed further before packaging for consumption.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

I claim:

1. A soap composition comprising saponified fatty acids with a carbon chain length of C4 to C22 or mixtures thereof, wherein the saponified fatty acids comprise at least caprylic fatty acid, capric fatty acid, or combinations thereof, wherein the saponified fatty acids consist of a mixture of caprylic fatty acid and capric fatty acid.

2. The soap composition of claim 1, wherein the saponified fatty acids further comprise natural oils selected from the group consisting of coconut oil, olive oil, tallow, tall oil fatty acids, sunflower oil, safflower oil, and combinations thereof.

3. The soap composition of claim 1, wherein the saponified fatty acids comprise omega-9 unsaturated fatty acids selected from the group of oleic acid, ricinoleic acid, and eurucic acid, and combinations thereof.

4. The soap composition of claim 1, wherein the soap composition is a hand soap, a liquid hand soap, a foaming liquid hand soap, a bath gel, an exfoliate cleanser, a cleaning wipe, a shampoo, a lotion, a cream, an industrial soap, or a lubricant.

5. The soap composition of claim 1, wherein the soap composition has a percent solids from about 18.0% (weight) to about 75% (weight).

6. The soap composition of claim 5, wherein the soap composition has a percent solids from about 30% (weight) to about 60% (weight).

7. The soap composition of claim 1 further comprising one or more additives from the group consisting of a detergent, a soap, a pigment, an adjuvant, a fragrance, and combinations thereof.

8. A method of manufacturing a soap composition comprising saponifying fatty acids with a carbon chain length of C4 to C22 or mixtures thereof, wherein the saponified fatty acids comprise at least caprylic fatty acid, capric fatty acid, or combinations thereof, and neutralizing the saponification reaction to an acceptable level of pH, wherein the saponified fatty acids consist of a mixture of caprylic fatty acid and capric fatty acid.

9. The method of claim 8, wherein the fatty acids comprise natural oils selected from the group consisting of coconut oil, olive oil, tallow, tall oil fatty acids, sunflower oil, safflower oil, and combinations thereof.

10. The method of claim 8, wherein the fatty acids comprise omega-9 unsaturated fatty acids selected from the group of oleic acid, ricinoleic acid, and eurucic acid, and combinations thereof.

11. The method of claim 8, wherein the acceptable level of pH is between about 8.8 and about 13.5.

12. The method of claim 8, wherein the acceptable level of pH is between about 9.5 and about 10.2.

13. The method of claim 8 further comprising adding one or more additives from the group consisting of a detergent, a soap, a pigment, an adjuvant, a fragrance, and combinations thereof.

14. A method of treating a superficial skin infection in a subject in need thereof comprising applying an effective amount of the soap composition of claim 1 to an area of the subject in need thereof, wherein the skin infection is associated with one or more of the group consisting of *Candida albicans, Pseudomonas aeruginosa, Staphylococcus aureus*, and *Aspergillus niger*.

15. The method of claim 14, wherein the area is selected from the group consisting of skin, hair, and fur.

16. The method of claim 14, wherein the skin infection is a diaper rash.

17. A method of treating a superficial skin infection in a subject in need thereof comprising applying an effective amount of the soap composition of claim 1 to an area of the subject in need thereof, wherein the skin infection is associated with one or more of the group consisting of *Candida albicans, Pseudomonoas aeruginosa, Staphylococcus aureus*, and *Aspergillus niger*.

18. The method of claim 17, wherein the area is selected from the group consisting of skin hair and fur.

19. The method of claim 17, wherein the skin infection is a diaper rash.

* * * * *